United States Patent [19]
Pickart

[11] Patent Number: 5,888,522
[45] Date of Patent: Mar. 30, 1999

[54] TISSUE PROTECTIVE AND REGENERATIVE COMPOSITIONS

[75] Inventor: Loren R. Pickart, Bellevue, Wash.

[73] Assignee: Skin Biology, Inc., Bellevue, Wash.

[21] Appl. No.: 917,446

[22] Filed: Aug. 22, 1997

Related U.S. Application Data

[60] Provisional application No. 60/023,908 Aug. 23, 1996.

[51] Int. Cl.$^6$ .............................. A61K 7/00; A61K 7/06; A61K 7/42; A61K 38/01
[52] U.S. Cl. ...................... 424/401; 424/59; 424/195.1; 424/520; 514/2; 514/6; 514/844; 514/880; 514/887; 514/801
[58] Field of Search .................................. 424/401, 423, 424/70.1, 520, 59; 514/2, 6, 801, 844, 880, 887

[56] References Cited

U.S. PATENT DOCUMENTS

| | | | |
|---|---|---|---|
| 3,758,682 | 9/1973 | Huber et al. | 530/369 |
| 4,053,630 | 10/1977 | Yu et al. | 424/289 |
| 4,156,737 | 5/1979 | Bertelli | 424/287 |
| 4,283,386 | 8/1981 | Van Scott et al. | 424/70 |
| 4,440,754 | 4/1984 | Sorenson | 424/140 |
| 4,461,724 | 7/1984 | Konishi | 260/112.5 |
| 4,503,047 | 3/1985 | Banfi et al. | 424/195.1 |
| 4,551,431 | 11/1985 | Pierce | 424/641 |
| 4,760,051 | 7/1988 | Pickart | 424/630 |
| 4,767,753 | 8/1988 | Pickart et al. | 514/18 |
| 4,863,897 | 9/1989 | Dede et al. | 424/630 |
| 5,164,367 | 11/1992 | Pickart . | |
| 5,382,431 | 1/1995 | Pickart | 424/401 |
| 5,554,375 | 9/1996 | Pickart | 424/401 |

FOREIGN PATENT DOCUMENTS

| | | |
|---|---|---|
| 066283 | 12/1982 | European Pat. Off. . |
| 189182 | 7/1986 | European Pat. Off. . |
| 190736 | 8/1986 | European Pat. Off. . |
| 288278 | 10/1988 | European Pat. Off. . |
| 450398 | 10/1991 | European Pat. Off. . |
| 2044265 | 10/1980 | United Kingdom . |
| 2097256 | 11/1982 | United Kingdom . |
| 88/08695 | 11/1988 | WIPO . |
| 88/08851 | 11/1988 | WIPO . |
| 89/12441 | 12/1989 | WIPO . |
| 91/03488 | 3/1991 | WIPO . |
| 91/05797 | 5/1991 | WIPO . |
| 91/07431 | 5/1991 | WIPO . |
| 91/12267 | 8/1991 | WIPO . |
| 91/14437 | 10/1991 | WIPO . |

OTHER PUBLICATIONS

Sorenson, "Some Copper Coordination Compounds and Their Antiinflammatory and Antiulcer Activities", *Inflammation* 1(3):317–331 (1976).

Sorenson et al., "Development of Copper Complexes for Potential Therapeutic Use", *Agents and Actions* 8:305–325 (1981).

Johnson et al., "Cytotoxic Chelators and Chelates Inhibition of DNA Synthesis in Cultured Rodent and Human Cells by Aroylhydrazones and by a Copper(II) Complex of Salicylaldehyde Benzoyl Hydrazone", *Inorg. Chem. Acta* 67:159–165 (1982).

Raju et al., "Ceruloplasmin, Copper Ions, and Angiogenesis", *J. Natl. Cancer Inst.* 69:1183–1188 (Nov., 1982).

Pickart et al., "Inhibition of the Growth of Cultured Cells and an Implanted Fibrosarcoma by Aroylhydrazone Analogs of the Gly–His–Lys–Cu(II) Complex", *Biochem. Pharm.* 32:3868–3871 (1983).

Pickart et al., "The Biological Effects and Mechanism of Action of the Plasma Tripeptide Glycycl–L–histidyl–L–l-ysine",*Lymphokines* 8:425–446 (1983).

Sorenson, "Copper Complexes: A Physiologic Approach to Treatment of Chronic Diseases", *Comprehensive Therapy* 11(4): 49–64 (1985).

Bergren et al. "Improved Survival Using Oxygen Free Radical Scavengers in the Presence of Ischemic Bowel Anastomosis", (*Am. Surg.* 54:333–336 (Jun., 1988).

Niwa, "Lipid Peroxides and Superoxide Dismutase (SOD) Induction in Skin Inflammatory Diseases, and Treatment with SOD Preparations", *Dermatologica* 179 S1: 101–106 (1989).

*Primary Examiner*—Thurman K. Page
*Assistant Examiner*—James M. Spear
*Attorney, Agent, or Firm*—Townsend and Townsend and Crew LLP

[57] ABSTRACT

Methods are provided for preparing compositions suitable for protecting irritated or damaged skin from further oxidative and biochemical damage and thus permitting natural healing processes to progress, for accelerating the rate of healing of burns and surgical wounds, for stimulating melanogenesis, and for increasing the size of hair follicles and the rate of hair growth. The compositions generally comprise complexation of peptone digests of various proteins with copper(II) salts, indium (III) salts, tin(II) salts and tin(IV) salts.

10 Claims, No Drawings

TISSUE PROTECTIVE AND REGENERATIVE COMPOSITIONS

RELATED APPLICATIONS

This application claims the benefit of U.S. Provisional Application Ser. No. 60/023,908, filed Aug. 23, 1996, and is continuation-in-part of U.S. Ser. No. 08/369,609, filed Jan. 6, 1995, now U.S. Pat. No. 5,554,375, which is a divisional of U.S. Ser. No. 07/954,620, filed Sep. 29, 1992, now U.S. Pat. No. 5,382,431, which are incorporated herein by reference.

BACKGROUND OF THE INVENTION

The treatment of irritated, damaged and wounded skin remains a major health problem despite the development of numerous medications. Furthermore, a major need exists for skin-care products and medicaments in less-developed countries, particularly in the tropics, where conditions such as inadequate health care, widespread skin fungal diseases, and the use of flammables such as kerosene for cooking and similar conditions give rise to high incidences of skin injury. For such countries, there is a critical need is to produce effective medicines that can be produced at very low cost using readily available materials. Many approaches to wound-healing currently being developed, such as the production of growth factor proteins by recombinant DNA methods, the use of pharmaceutical drugs with wound healing attributes, and occlusive dressings for wounds, will remain beyond the economic reach of patients in these countries for the next few decades.

In more developed countries, increasing pressures for cost-containment in medical services also necessitate the development of low-cost products for skin care and pharmaceuticals for wound healing. Procedures such as hospitalization for the treatment of venous stasis ulcers, while therapeutically effective, are today rarely permitted by medical insurance providers and outpatient treatments are increasingly common. While many alternate therapies being developed, such as the use of growth factors to accelerate skin repair, these also promise to be relatively high cost therapies.

Delayed healing or incomplete healing in humans and other animals causes additional pain and suffering for the patient and markedly increases wound complications and medical costs, and often the wound continues as a chronic sore that requires extensive attention and medical care to control infection and tissue necrosis. Even when such wounds finally heal, the wound area is frequently devoid of the ability to respond to tactile stimulation and is often filled with excessive deposits of immature collagen that produces permanent scarring. The urgent need for improved wound-healing compositions also extends to wounds generated by surgical procedures. The success of surgical procedures, especially in very ill or elderly patients, is typically a function of the adequacy and speed of post-surgical healing.

Another aspect that can impair the normal healing response is excessive inflammation of injured or wounded skin. While the inflammatory process and its concomitant influx of white cells into the afflicted area are an integral part of the natural healing process, in some cases the inflammatory process becomes excessive and delays healing. The wounded tissue becomes locked in an early phase of the healing process and cannot proceed to completion. In such instances, compounds with anti-inflammatory activities are used to allow the process to proceed normally.

One promising approach for the therapeutic treatment of the clinical problems associated with inflammation and impaired wound healing has been the use of metal ions complexed to organic molecules or amino acids, amino acid derivatives and peptides. Some of these complexes possess anti-inflammatory activity, while others possess both anti-inflammatory activity and healing actions. Yet other complexes reportedly possess hair growth stimulating actions in addition to anti-inflammatory and/or healing activities.

The use of copper salts or complexes as anti-inflammatory agents for the healing of stomach ulcers in the treatment of patients suffering from acute or chronic arthritis dates back to the 1940's and 1950's (see, e.g., reviews by Sorenson, *Inflammation* 3:317–331 (1976); *Agents and Actions* 8:305–331 (1981), and *Comprehensive Therapy* 11:49–64 (1985)). The use of copper salts and complexes, such as copper-salicylate complex, seems to have been abandoned, apparently due to the early promise of the steroidal anti-inflammatories, such as hydrocortisone. Other complexes of copper with amino acids (tryptophan, lysine), with non-steroid anti-inflammatory drugs (indomethacin, ketoprofen, acetylsalicylic acid) or with fatty acids (oleic, lauric and caprylic acids) have been studied but, despite their promise, were rarely developed beyond the preclinical phases due to problems of irritation, toxicity, and inadequate efficacy.

While many copper-complexes have been reported to possess anti-inflammatory properties, a more limited group have been reported to also possess healing actions. Heintze (U.S. Pat. No. 4,123,511) reported that a copper oleate complex had anti-inflammatory and skin healing activity. Sorenson (U.S. Pat. No. 4,440,754) describes the use of complexes of copper(II) salts and amino acids, such as tryptophan or lysine, or with organic molecules such as 3,5-diisopropylsalicylic acid, acetylsalicylic acid or salicylic acid, to prevent and heal gastrointestinal ulcers. Using a wound-healing model, Townsend and Sorenson (Sorenson et al., *Agents and Actions* 8:305–325 (1981)) found salicylate-copper to accelerate the rate of healing and improve the quality of healing of surgically-induced ulcers in rats. Also, Sorenson writes (ibid. and *Inflammation* 3:317–331 (1976)) that Townsend demonstrated that copper(II)-(tryptophan)$_2$ increased the rate of ulcer healing in a surgically-induced ulcer model. The increased healing was purportedly due to a more rapid re-epithelialization of the wound and an increase in the quantity and quality of the collagen. Fine collagen fibers in a normal orientation developed in treated animals, in contrast to non-treated animals in which the new collagen was very dense and composed of thick, wavy disoriented bundles, resembling scar tissue.

Federici and Bertolotto (EP 450,398 and IT 9,019,948) reported that chondroitin sulfate-copper(II) complexes possessed anti-inflammatory activity. European Patent No. EP 66,283 discloses "eustatic" compositions which contain a non-toxic metal ion (including copper) and a glycosaminoglycan of hyaluronic acid or chondroitin sulfate useful as a cicatrizant (wound healing by closure).

UK Patent Application GB 2 044 265 describes metal complexes (including copper) of adenosine triphosphate as aiding the recovery of bone tissue in cases of fractures as well as in osteoporosis and bone cysts.

Konishi (U.S. Pat. No. 4,461,724) reports that the tetrapeptide Gly-Ser-His-Lys and peptides of related structures possess anti-inflammatory and healing actions when complexed with metals such as ionic copper and zinc.

Yu (U.S. Pat. No. 4,053,630) discloses the use of cysteic acid and its derivatives cysteine sulfinic acid or homocysteic acid, chelated to metal ions such as ferric, cupric, zinc or aluminum, to form compositions that alleviate symptoms of diseases characterized by defects of keratinization and achieved a remission of ichthyosis, dandruff and acne. Bertelli (U.S. Pat. No. 4,156,737) suggests that copper complexes of p-aminomethyl-benzene-sulfonamide possess healing and protective effects on skin burns. Van Scott (U.S. Pat. No. 4,283,386) teaches that metallic (copper, zinc, or aluminum) salt forms of cysteic acid, cysteine sulfinic acid and homocysteic acid have therapeutic actions that produce remissions of dry and broken skin, keratoses, warts and palmar and plantar hyperkeratosis.

Niwa (*Dermatologica* 179 S1: 101–106 (1989)) and Bergren et al. (*Am. Surg.* 54:333–336 (1988)) found that the anti-inflammatory protein Cu,Zn-superoxide dismutase also acts to enhance healing processes.

Pickart (PCT Publications WO 91/14437, WO 91/12267, WO 91/05797, WO 91/03488, WO 89/12441, WO 88/26448, WO 88/08851, EP Patents EP 190,736, EP 189,182; and U.S. Pat. No. 4,767,753) describes the synthesis and use of metal complexes of Gly-L-His-L-Lys as anti-inflammatory and healing agents.

A number of metal complexes have been used to promote hair growth. Yamashiki (Japan Pat. 70018997) used a complex of copper-pantothenate to purportedly promote growth of hair roots and promote skin functions. Morelle (U.K. Pat. GB 2097256, DE Pat. 32212448) used amino acid derivatives (N-butyryl amino acids) complexed with copper and other metals for cosmetic and therapeutic purposes, including use as hair and skin stimulants. Banfi et al. (U.S. Pat. No. 4,503,047) disclose a composition containing primarily one or more sulfur-containing amino acid(s) and copper(II) ions plus smaller amounts of allyl isothiocyanate and rhodanide ions to produce hair growth stimulating actions. Pickart (WO 91/07431, 88/08695 and EP 288,278) found a number of metal complexes of derivatives of Gly-L-His-L-Lys to increase hair follicle size and the rate of hair growth.

Despite the therapeutic promise of the above-mentioned metal complexes, toxicity and tissue irritation occur with many metal complexes (see, e.g., Johnson et al., *Inorg. Chem. Acta* 67:159–165 (1982); Pickart et al., *Biochem. Pharm.* 32:3868–3871 (1983); and Pickart et al., *Lymphokines* 8:425–446 (1983)). For example, while copper-salicylate complexes and numerous copper-salicylate analogs possess anti-inflammatory activities, other salicylate analogs such as the copper(II) complex of salicylaldehyde benzoyl hydrazone are highly toxic to tissues. Similarly, copper(II)-Gly-L-His-L-Lys supports cellular viability and possesses anti-inflammatory and healing actions, yet close synthetic aroylhydrazone analogs of its copper-binding region are extremely toxic to cells and tissues.

Another problem with copper complexes for therapeutic use concerns the binding affinity of copper ion to the complexing molecule. While a defined copper-complex can be synthesized, its therapeutic use places it in the physiological milieu of the tissues where a plethora of literally hundreds of compounds compete for binding to the copper ion, which can form electrostatic bonds to as many as six separate molecules. If the copper is removed from the complex and becomes loosely-bound, then tissue irritation occurs (see Raju et al., *J. Natl. Cancer Inst.* 69:1183–1188 (1982)).

Further complications arise when such metal complexes are formulated into carrier creams or ointments. Various chemicals are added to the formulations to increase adherence to skin and wound surfaces and to enhance the penetration of the complexes into the target tissue. Yet, since many of these substances also bind to the metals, the expected therapeutic benefits may be nullified or significantly attenuated. Also, detergents such as sodium dodecyl sulfate are used to help blend oil and water phases of the emulsions and stabilize the formulations. However, such detergents are themselves tissue irritants that can delay healing.

Another problem encountered with many of the metal complexes intended for therapeutic use is that they cannot be heat-sterilized; hence, to meet safety requirements, high concentrations of antimicrobial chemicals must be added during manufacture to inhibit the growth of microorganisms and the transmission of viruses. These antimicrobial agents may also inhibit the viability and function of a host's cells such as macrophages and fibroblasts that are involved in the maintenance and repair of skin and other tissue, and thus these agents may retard the healing response.

What are needed in the art are compositions useful in tissue protection, tissue healing, and/or stimulating hair growth, which compositions could be conveniently produced and at low cost. Preferably, the compositions could be sterilized without loss of bioactivity and could be formulated for topical application without the use of detergents or other potentially irritating compounds. Even more preferably, the compositions would be generally recognized as safe by regulatory agencies and thus could be used with minimal safety concerns and regulatory barriers. Quite surprisingly, the present invention fulfills these and other related needs.

SUMMARY OF THE INVENTION

The present invention provides compositions and methods for accelerating the healing of topical wounds and skin irritation, for protecting skin from damaging effects of oxidation, and for increasing the size of hair follicles and the rate of hair growth in warm-blooded animals. The compositions useful in these methods, including pharmaceutical compositions, are prepared from peptones complexed with an ionic transition metal.

Thus, in one aspect the invention provides methods for preparing the pharmaceutical compositions useful in accelerating the healing of topical wounds or increasing hair follicle size and hair growth in a warm-blooded animal. A peptone digest is combined with an amount of an aqueous solution of transition metal salt sufficient to induce a precipitate. Typically, the peptone digest is prepared from casein, collagen, elastin, meat products, silk protein, soybean protein, and the like, and the ionic transition metal is selected from copper(II), indium (III), tin(II) and tin(IV).

The resulting precipitate is composed of complexes of the hydrophobic peptides from the peptone and the metal. The precipitate of peptone-metal complex is then isolated, such as by centrifugation, and then formulated as desired for the intended use and mode of administration. Typically the complex is combined with a pharmaceutically acceptable carrier to form a cream or lotion, in a concentration of from about 5% to about 25% peptone-metal complex or more. The preparation may be sterilized or pasteurized, as desired, without destroying the healing or hair-growth stimulating activity of the peptone-metal complex.

In other embodiments the invention provides methods for enhancing the recovery of skin of a warm-blooded animal from wounds, such as surgical incisions, burns, inflammation or minor irritation due to oxidative damage, etc. The methods comprise administering to the skin wound or irritation a therapeutically or, in some cases a prophylactically effective amount of a composition which comprises the peptone-ionic transition metal complex. Due to the increased adhesiveness of the compositions of the invention re-application to the skin is minimized compared to other topical healants and formulations.

Yet other embodiments relate to compositions and method for increasing hair follicle size and the rate of hair growth in warm-blooded animals, such as humans. The methods comprise administering to the skin in the area in which hair growth is desired an amount of peptone-metal complex sufficient to increase hair follicle size and the rate of hair growth in said animal. Typically, the composition will be administered topically as a cream, and will be applied on a daily basis until hair growth is observed and for a time thereafter sufficient to maintain the desired amount.

DESCRIPTION OF THE SPECIFIC EMBODIMENTS

Compositions and methods are provided by the present invention for topical skin treatments to protect damaged skin and thereby allow natural healing processes to proceed, to enhance tissue regenerative processes in the skin of warm blooded animals, and to stimulate hair growth in warm blooded animals. The composition are formed by the complexation of enzymatic protein digests and ionic transition metals such as copper, indium or tin. Methods are provided for improving the recovery of damaged skin, accelerating the healing of burns or surgical incisions, and stimulating hair growth in warm-blooded animals.

The peptone-metal complexes of the present invention are prepared from enzymatic digests of proteins. Peptones are generally comprised of intermediate polypeptide products and mixtures of small peptides, formed in partial hydrolysis of proteins. Among the types of enzymatic protein digests useful in the invention are digests of soybean protein, casein, collagen, elastin, meat products (e.g., PRIMATONE), such as beef, liver, silk protein and so forth. By peptone digest is meant that the protein is degraded by enzymatic digestion according to well known procedures, such as described in Remington's Pharmaceutical Sciences, Mack Publishing Co., Easton, Pa. pp. 428–429 (1975), which is incorporated herein by reference, using enzymes such as papain, etc. Many peptone digests are widely available commercially, such as from Sigma Chemical Company, St. Louis, Mo.

To produce the complexes useful in the present invention, the peptone digests are complexed with one or more ionic transition metals, such as copper, indium, tin, zinc, or the salts thereof, such as sulfate, acetate, phosphate, etc. In one method for preparing the peptone-metal complex, a peptone is dissolved in warm water (about 40° C.) at a concentration of about 5 to 50% (weight/volume), then mixed with a aqueous solution of a metal salt (copper(II) chloride, tin(II) chloride, tin(IV) chloride, indium(III) chloride, or zinc(II) chloride) at a salt concentration of about 10 to 50% (w/v), more preferably about 20% (w/v). The volume of metal salt solution added is that amount needed to induce a copious precipitate in the solution (about 20 to 50% of the initial volume of in the case of soybean peptone), after the pH is adjusted to between about pH 6 to pH 7 to induce maximum formation of precipitate. The precipitate contains substantial amounts of hydrophobic peptides, plus a small amount, generally about 1–10%, of the metal salt complexed to the peptides. By complexed is meant that the peptides and metal ions form electrostatic bonds, although this mechanism is offered by way of possible explanation only and not by way of limitation.

Isolation and purification of the peptone-metal complexes can then be effected by any suitable separation or purification procedure such as, for example, filtration, extraction, centrifugation, crystallization, or a combination of these procedures. Specific illustrations of suitable separation and isolation procedures can be had by reference to the examples hereinbelow. However, other equivalent separation or isolation procedures could, of course, also be used.

In an alternative method of preparation, the peptones and copper chloride are directly combined in warm water (about 40°–60° C.) at concentrations which are the final concentrations desired for the formulation to be applied to the host. The pH of the mixture is adjusted (with sodium hydroxide or the like) to a pH between 6.0 and 7.0, and other aqueous components, as desired, are added, followed by blending in of carriers, smootheners, etc. for preparing a final formulation. This method avoids the necessity of a centrifugation step while producing formulations at desired copper-peptone final concentrations, which formulations have been found to be more effective at lower copper concentrations.

The peptone-metal complexes of the invention may be administered for a variety of therapeutic, prophylactic or cosmetic uses to humans or in veterinary applications to other warm-blooded animals. Among veterinary animals particularly well suited for treatment with the present compositions are species of equine, bovine, porcine, ovine, caprine, canine, avian, feline, etc.

The compositions and pharmaceutical preparations thereof are intended for local, topical, oral or parenteral (e.g., subcutaneous injection) administration for prophylactic and/or therapeutic or a cosmetic treatment regimen, to facilitate natural healing and enhance tissue regenerative processes. Preferably, the compositions, including pharmaceutical compositions, are administered are administered locally, e.g., topically, as a paste, cream, salve, lotion, gel, spray or the like.

For administration to warm-blooded animals, the peptone-metal compositions will typically be sterilized and incorporated in pharmaceutical or veterinary formulations. Compositions which comprise the peptone-metal complexes can be sterilized by conventional, well known sterilization techniques, e.g., boiling or pasteurization, without substantially adversely affecting the biological activity of the peptone-metal complexes. The compositions may contain pharmaceutically acceptable auxiliary substances as required to approximate physiological conditions and as necessary to prepare compositions for convenient administration, such an pH adjusting and buffering agents, and delivery vehicles. Actual methods for preparing pharmaceutically administrable compounds will be known or apparent to those skilled in the art and are described in detail in, for example, Remington's Pharmaceutical Science, infra.

Depending on the intended mode of administration and the intended use, the compositions may be in the form of solid, semi-solid, or liquid dosage forms, such, for example, as powders, granules, crystals, liquids, suspensions, liposomes, pastes, creams, salves, etc., and may be in unit-dosage forms suitable for administration of relatively precise dosages. The compositions may include a conventional pharmaceutical carrier or excipient and, in addition, may include other medicinal agents, growth factors, wound sealants, carriers, etc., as further described below.

For semi-solid compositions, as would be appropriate for pastes and creams intended for topical administration, the peptone-metal complexes can be provided separately or may be compounded with conventional nontoxic carriers such as, for example, aloe vera gel, squalane, glycerol sterate, polyethylene glycol, cetyl alcohol, stearic acid, and propylene glycol, among others. Such compositions may contain about 5–100% active ingredient, more preferably about 5–25%. Thus, the final concentration of copper or other metal in a formulation can range from about 0.1 or 0.15% (w/v) up to 0.4 to 0.8% or 1.6%, and in some instances up to 2 to 5% or more, although it will typically be desirable to employ the lowest final concentration of copper as possible which achieves the desired effect. The concentration of the peptone-metal complexes in these formulations can vary widely, and will be selected primarily by intended use, viscosities, etc., in accordance with the particular mode of administration selected. Actual methods of preparing such dosage forms are known, or will be apparent, to those skilled in this art; for example, see Remington's Pharmaceutical Science, 17th ed., Mack Publishing Company, Easton, Pa. (1985), which in incorporated herein by reference. The composition or formulation to be administered will, in any event, contain a quantity of the peptone-metal complexes sufficient to achieve the desired therapeutic or prophylactic effect in the subject being treated.

The compositions of the invention are administered to a warm-blooded animal, such as humans, already suffering from a wound, oxidative skin damage, inflammatory skin lesions, as described above, in an amount sufficient to allow the healing, protective or melanogenic process to proceed more quickly than if the host were not treated. In the case of an animal suffering from decreased hair follicle size and impaired hair growth, the compositions of the invention are administered in an amount sufficient to increase hair follicle size and the rate of hair growth. The use of peptone-metal compositions to stimulate melanogenesis while providing protection to the skin is described in U.S. Pat. No. 5,698,184 and incorporated by reference herein. Amounts adequate to accomplish these effects are defined as a "therapeutically effective doses." Amounts effective for this use will depend on the severity of the wound, sore, etc., in the case of wound healing, the extent of decreased follicle size in the case of impaired hair growth, or the extent of melanogenesis and skin protection desired, as well as the general state of health of the patient being treated, but generally range from about 1 mg to about 50 mg per day of peptone-metal complex per day per square centimeter of wound site, with dosages of from about 10 mg to about 25 mg per day per square centimeter of wound site being more commonly used. Maintenance dosages over a prolonged period of time may be adjusted as necessary. For veterinary uses higher levels may be administered as necessary. Determining actual amounts of the peptone-metal complexes necessary to treat a particular condition as described herein will be through standard empirical methods well known in the art. A representative lotion formulation for application to the skin comprises, in approximate amounts (final concentrations, w/v %): water, 62.9; cetyl alcohol, 5.0; stearic acid, 5.0; ARLACEL 165, 7.0; LEXOL EHP, 4.0; squalene, 5.0; copper chloride-2H$_2$0, 0.40; soybean peptone, 6.0; mineral oil, 3.0; allantoin, 0.5; GERMABEN-II-E, 1.0; herbal fragrance, 0.1; aloe vera powder, 0.1; vitamin A-D, 0.01; vitamin E, 0.01.

In prophylactic applications compositions containing the peptone-metal complexes are administered to a host susceptible to or otherwise at risk of skin lesions or similar damage, to enhance the host's own wound healing or anti-oxidative capabilities. Such an amount is defined to be a "prophylactically effective dose." In this use, the precise amounts again depend on the host's condition and general state of health, but generally range from about 0.1 mg to about 10 mg per day per square centimeter of skin, more commonly from about 1 mg to about 3 mg per cm$^2$ of skin per day. Single or multiple administrations of the compositions can be carried out.

The peptone-metal complexes of the invention may be administered in relatively large amounts without serious side effects, although indiscriminate use may produce discoloration of the skin. In instances where the compositions are administered to inhibit oxidative or biochemical damage to the skin or to those suffering from only mild or irritation or inflammation of the skin, the dose may be adjusted accordingly to lower maintenance levels.

The compositions of the invention, including pharmaceutical compositions, may be administered alone or as adjunct therapy or prophylaxis. The peptone-metal compositions can be used in combination with other factors found to improve other aspects of healing, skin protection or melanogenesis, etc. In this manner, a synergistic effect may be attained that yields a clinical efficacy greater than that realized with any single factor. Further, while the compositions described herein stimulate a spectrum of healing processes, clinical wounds may differ considerably in their properties and healing patterns, leading one to utilize a combination of a composition described herein and another factor. For example, nerve regeneration is defective in many burns and thus one can add a specific nerve growth factor to the composition to enhance nerve regrowth into the burn area. Examples of factors with other reported healing properties include epidermal growth factor, fibroblast growth factor, nerve growth factor, transforming growth factors, angiogenic growth factors, heparin, fibronectin, fibrin, platelet-derived growth factor, enzymatic superoxide dismutase, extracts of blood or factors from the blood, and other similar factors.

The following examples are offered by way of illustration, not by way of limitation.

EXAMPLE I

Preparation of Active Peptone-Metal Complexes

This Example describes methods used in the preparation of the peptone-metal complexes having biological activities described further below.

Soybean peptone was obtained from Sigma Chemical Company, St. Louis, Mo. (type IV, number P 0521), as was cupric chloride hydrate (no. C 6641). Indium (III) chloride, 99% pure; tin (II) chloride, 99% pure; and tin (IV) chloride, 99% pure were obtained from Aldrich Chemical Company, Milwaukee, Wis.

Soybean peptones (enzymatic digests of soybean protein) were dissolved in warm water (40° C.) at a concentration of 20% (weight/volume), then mixed with a aqueous solution of a metal salt (copper(II) chloride, tin(II) chloride, tin(IV) chloride, indium(III) chloride, or zinc(II) chloride) at a salt concentration of 20% (w/v). The amount of volume of salt solution added was that amount needed to induce a copious precipitate in the solution, or about 20 to 50% of the initial volume of soybean peptone, after the pH was adjusted with sodium hydroxide to induce maximum formation of precipitate (between 6.0 to 7.0). The precipitate contained substantial amounts of hydrophobic peptides, plus a small amount (3.8–4.2% by assay) of the metal salt complexed to the peptides.

The precipitates were removed by centrifugation at 10,000 G for 20 minutes, then processed as a wet paste into further products. The sticky paste can be applied directly to the skin or is formulated into skin creams and lotions at concentrations of usually 5 to 20% (w/w) although higher concentration are also effective.

The soybean peptone-copper complexes are used as skin protective agents that serve as a skin barrier over damaged or irritated skin. The hydrophobic peptides adhere to the skin and form a protective barrier, while the complexed copper serves to impart a antioxidant activity to the mixture. Damaged or irritated skin healed strikingly faster after treatment with such a composition.

As described further below, the peptone-copper, peptone-tin and peptone-indium complexes were used to promote hair growth and the enlargement of hair follicles. In hair growth models in mice, application of these complexes to the skin produced a marked stimulation of hair growth after 10 to 14 days.

Other types of enzymatic protein digests such as those of casein, collagen, elastin, meat products, silk protein and the like, and other metal salts of the metals, such as sulfate, acetate, phosphate and so forth would be expected to work similarly.

EXAMPLE II

Healing of Surgical Wounds with Peptone-Copper Complex

This Examples describes the use of a paste prepared with the peptone-copper complex to hasten the healing of surgical incision wounds in animals.

Surgical incisions (1.25 cm) were made on the backs of anesthetized, 35 gram, Swiss-Webster mice. Immediately after surgery and 24 hours later, the wounds were covered with a thin film of the paste containing the active peptone-copper complex in Example I above. Control wounds were untreated. As seen in Table 1, wounds treated with the active peptone-copper complex healed faster than control wounds. Since rapidly healing wounds tends to contract and become more rounded, the healing activity can be related to the length of the wound after 15 days. Each group consisted of 12 mice.

TABLE 1

Effect of peptone-copper complex on incision length.

| Test group | Length of wound after 15 days (cm.) |
| --- | --- |
| Control | 0.81 ± 0.10 |
| Peptone-copper complex | 0.20 ± 0.13 |

EXAMPLE III

Healing of Surgical Skin Defects

This Example demonstrates faster healing of skin lesions in animals by administering the peptone-copper complexes topically.

Surgical skin defects were created by the removal of skin (circular, 1.25 cm. diameter, area=1.22 square cm.) from the backs of anesthetized mice. Immediately after surgery and 24 hours later, the wounds were covered with a thin film of the paste containing the active peptone-copper complex in Example I above. Control wounds were untreated. As shown in Table 2, wounds treated with the active peptone copper complex healed faster than control wounds. The healing activity can be related to the remaining unhealed area of the wound after 15 days. Each group consisted of 12 mice.

TABLE 2

Effect of peptone-copper complex on healing of surgical defect.

| Test group | Wound area after 15 days (cm$^2$) |
| --- | --- |
| Control | 0.27 ± 0.14 |
| Peptone-copper complex | 0.02 ± 0.01 |

EXAMPLE IV

Healing of Burn Wounds with Peptone-Copper Complex

This Example demonstrates the increased healing of burn wounds in animals using the peptone-copper compositions applied topically.

Second-degree burns were induced on the shaved backs on anesthetized mice by placing a circular (1.25 cm diameter, wound area=1.22 cm$^2$) brass rod (temperature 100° C.) in contact the skin for 7 seconds. Immediately after burning, and 24 and 48 hours later, the wounds were covered with a thin film of the paste containing the active peptone-copper complex of Example I above. Control wounds were untreated. Wounds were photographed at 5 day intervals and the wound areas calculated from the photographs by plainometry. Burns treated with the active peptone copper complex showed less post-burn inflammation and healed markedly faster than untreated control wounds. Each group consisted of 12 mice.

TABLE 3

Effect of peptone-copper-complex on burn wounds.

| Test group | Area of wound after 15 days (cm$^2$) |
| --- | --- |
| Control | 0.84 ± 0.10 |
| Peptone-copper complex | 0.24 ± 0.13 |

EXAMPLE V

Healing of Burn Wounds with Peptone-Copper Complex in a Cream Base

This Example demonstrates that burns treated with the active peptone-copper complex in a topical cream ointment showed a dose-response increase in the degree of healing.

Burns were induced as in the Example IV. An application cream was devised containing 55% (by weight) aloe vera gel, 12% squalane, 12% glycerol stearate, 5% PEG-100 and 4% cetyl alcohol. To this basic cream various concentrations of the copper-peptone composition were added (2.5%, 5%, 10% and 20%) and the mixtures blended. Immediately after burns were applied to the animals, and 24 and 48 hours later, the wounds were covered with a thin film of the cream containing the active complex. Control wounds were treated with the basic cream only. Wounds were photographed at 5 day intervals and the wound areas calculated from the photographs by plainometry.

The results showed that burns treated with the active peptone copper complex had a dose-response increase in the degree of healing. At the lowest dose, 2.5% concentration, the wounds appeared less inflamed even though there was no significant acceleration of healing. Each group consisted of 10 mice.

TABLE 4

Effect of peptone-copper complex on burn wounds.

| Test group | Wound area after 15 days (cm$^2$) |
|---|---|
| Control | 0.71 ± 0.17 |
| 2.5% Peptone complex | 0.74 ± 0.19 |
| 5% Peptone complex | 0.44 ± 0.05 |
| 10% Peptone complex | 0.38 ± 0.14 |
| 20% Peptone complex | 0.29 ± 0.10 |

EXAMPLE VI

Reduction in Post-Burn Inflammation of Skin

This Example demonstrates the ability of peptone-copper complex to reduce inflammation associated with mild skin burns.

Very mild thermal burns were induced on the shaved backs of anesthetized mice (12 mice in each group) by a placing a circular (1.25 cm diameter, irritated area =1.22 cm$^2$) brass rod (60° C.) in contact the skin for 5 seconds. This produced a mild skin irritation characterized by redness and swelling, but rarely a loss of skin tissue. Immediately after inducing the thermal injury, the irritated area was covered with a thin film of the paste containing the active complex in Example I above. Control wounds were untreated. Wounds were observed at daily intervals. At day 3, the untreated thermal injuries were still reddish and swollen while the treated skin had a nearly normal appearance, with only minimal reddishness and swelling.

EXAMPLE VII

Pasteurization of Active Peptone-Copper Composition

Pasteurization consists of heating a solution to 160 degrees for 30 minutes which kills all but the hardiest microorganisms. For this test, 10 grams of soybean peptone hydrolysate was complexed with copper chloride by the methods described above in Example I. After the addition of the copper chloride solution to the solution of soybean peptone hydrolysate, the resultant solution was thoroughly mixed, then heated to 160° F. for 30 minutes. After cooling to room temperature, the active composition was prepared by the methods described above, then applied to surgical incision wounds in mice in the manner described in Example I. Healing activity was similar to that observed with unpasteurized active composition.

TABLE 5

Effect of pasteurization on active complex.

| Test group N = 6 | Length of wound after 15 days (cm) |
|---|---|
| Control | 0.86 ± 0.16 |
| Unpasteurized Active complex | 0.26 ± 0.13 |

TABLE 5-continued

Effect of pasteurization on active complex.

| Test group N = 6 | Length of wound after 15 days (cm) |
|---|---|
| Pasteurized Active Complex | 0.24 ± 0.15 |

EXAMPLE VIII

Sterilization of Active Composition by Boiling

This Example demonstrates that the peptone-copper complex can be sterilized by boiling and yet retains substantially all of the activity of the unsterilized formulation. This presents considerable advantage by avoiding the necessity of include sensitizing antimicrobial agents in the compositions.

Sterilization by boiling kills virtually all microorganisms. For this test, 10 grams of soybean peptone hydrolysate were complexed with copper chloride by the procedure described above in Example I. After adding the copper chloride solution to the solution of soybean peptone hydrolysate, the resultant solution was thoroughly mixed, then heated to boiling for 5 minutes. After cooling to room temperature, the active composition was prepared as described above in Example I, then applied to surgical wounds in mice in the manner described in Example II. The healing activity observed with the sterilized peptone-copper complex was similar to results obtained with unpasteurized active compositions.

TABLE 6

Effect of pasteurization on active complex.

| Test group N = 6 | Length of wound after 15 days |
|---|---|
| Control | 0.90 ± 0.22 |
| Unpasteurized Active complex | 0.28 ± 0.15 |
| Pasteurized Active Complex | 0.28 ± 0.09 |

EXAMPLE IX

Adherence of Peptone-Copper Cream to Skin

This Example describes the use of the peptonecopper active complex to improve the adherence of skin creams to the surface of the skin. The peptone-copper complex creams can thus be used to as an effective wound sealant, or to facilitate delivery of other growth factors and compounds to wounds, lesions and the like.

A basic cream composed of 55% (by weight) aloe vera gel, 12% squalane, 12% glycerol stearate, 5% PEG-100 and 4% cetyl alcohol was prepared. A second cream comprised the first cream (50 grams) into which 10 grams of a copper-peptone composition were blended. Samples (0.5 grams) of each cream were spread evenly within a 3 cm diameter circle on the back of the hands (first cream on one hand, the second cream on the other) of ten (10) human volunteers. The samples were allowed to "set" for three minutes, then washed off under a stream of running water set at a constant flow rate. The time to "wash-off" of the cream was the time required to remove the cream from at least 90% of the covered surface. In general, the control cream washed off within 4 to 9 seconds (average 6 seconds) while the cream containing the peptone-metal complex washed off between 22 and 65 seconds (average 34 seconds).

If the applied copper-peptone cream (the second cream) was applied to skin and allowed to "set" for one hour, it appeared to bond somewhat to the skin surface and characteristic blue-green color of the cream could only be removed by vigorous scrubbing of the skin with soap. In contrast, the control cream (the first cream) could still be easily washed from the skin after setting for one hour.

Similar results on increasing cream adherence to the skin were found for tin-peptone compositions and indium-peptone compositions

EXAMPLE X

Stimulation of Hair Growth by Injection

This Example describes the use of compositions containing peptone-copper complexes to stimulate the growth of hair follicles in warm blooded animals.

The model used in this test was a mouse model that has been found to successfully predicts the therapeutic response in humans (see, e.g., U.S. Pat. No. 5,118,665, which is incorporated herein by reference). Hair growth in mammals proceeds through actively growing stages (anagen) followed by dormant stages (telogen). The test method generally involves applying the hair-growth stimulant to the skin of mice in telogen phase. Female, Swiss-Webster mice begin a telogen phase at about 45 days of age that lasts until about 90 days of age. After application of the active substance, enhanced hair growth is noted within 10 to 14 days. For this test, mice 50 days of age were used.

Peptone compositions containing copper(II), indium(III), tin(II) and tin(IV) were tested. For testing, the compositions were mixed with saline (5% peptone composition and 95% physiological saline by weight). Mice were shaved, then 0.05 milliliter of the mixture was infiltrated immediately below the skin by injection. Control mice were injected with an equal volume of saline. Each group contained 10 mice. After 14 days, the groups were compared. The percentage of mice with hair growth at the injection site and the relative strength of the hair growth response (on a scale of 1 to 5 where 1 is barely noticeable growth and 5 is very strong hair growth) were determined.

The results, shown in Table 7, indicate that all composition were active hair growth stimulants, with peptone-tin(II) complexes being the most effective agent.

TABLE 7

Stimulation of Hair Growth by Peptone-Metal Complexes.

|  | Percent with hair growth at injection site | Average intensity of hair growth |
|---|---|---|
| Control mice | 0 | 0 |
| Peptone-copper (II) | 100 | 2.5 |
| Peptone-indium (II) | 80 | 2.5 |

TABLE 7-continued

Stimulation of Hair Growth by Peptone-Metal Complexes.

|  | Percent with hair growth at injection site | Average intensity of hair growth |
|---|---|---|
| Peptone-tin (II) | 100 | 4.5 |
| Peptone-tin (IV) | 100 | 4.0 |

EXAMPLE XI

Stimulation of Hair Growth by Topical Application

The model used in this test is as in Example X except that the active substance was applied topically to the mouse skin. Peptone compositions containing copper(II), indium(III), tin(II) and tin(IV) were tested. For testing, the compositions were mixed with saline (25% peptone composition and 75% physiological saline by weight) to form a slurry. Mice were shaved, then 0.20 grams of the mixture applied to the shaved area as smoothly as possible. Control mice were swabbed with saline. Each group contained 10 mice. After 14 days, the mouse groups were compared. The percentage of mice with hair growth in the center of the shaved area and the relative strength of the hair growth response (on a scale of 1 to 5 where 1 is barely noticeable growth and 5 is very strong hair growth) were determined. All composition were active with tin(II) being the most effective agent.

TABLE 8

Topical Application of Peptone-Metal Complexes to Stimulate Hair Growth.

|  | Percent with hair growth in center of shaved area | Average intensity of hair growth |
|---|---|---|
| Control mice | 10 | 0.2 |
| Peptone-copper (II) | 90 | 2.0 |
| Peptone-indium (II) | 80 | 2.0 |
| Peptone-tin (II) | 100 | 4.0 |
| Peptone-tin (IV) | 100 | 3.0 |

It is evident from the above results that the subject invention provides compositions of peptone-metal complexes for topical skin, wound and surgical treatments to protect damaged skin and facilitate natural healing processes, to enhance tissue regenerative processes in the epidermis, and to stimulate hair growth in warm blooded animals. The invention also provides economical methods for preparing and formulating the compositions for topical administration.

All publications and patents mentioned in this specification are indicative of the level of skill of those skilled in the art to which this invention pertains. All publications and patents are herein incorporated by reference to the same extent as if each individual publication or patent was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for preparing a topical composition useful for accelerating the healing of topical wounds, protecting skin from oxidative damage, stimulating melanogenesis, increasing hair follicle size and rate of hair growth in a warm-blooded animal or as a cosmetic, which comprises combining a peptone digest with an aqueous solution of an ionic metal salt and heating under conditions sufficient to form a peptone-metal complex; and admixing the peptone-metal complex with topically acceptable carriers for use as said topical composition.

2. The method of claim 1, further comprising the step of sterilizing or pasteurizing the peptone-metal complex.

3. The method of claim 1, further comprising the steps of precipitating the peptone-metal complex and isolating said precipitated complex before combining it with the topically acceptable carrier.

4. The method of claim 1, wherein the peptone-metal complex is combined with a topically acceptable carrier to form a cream or lotion.

5. The method of claim 1, wherein the concentration of the peptone-metal complex in the topical composition is about 5% to 25%.

6. The method of claim 1, wherein the peptone digest is prepared from casein, collagen, elastin, meat products, silk protein, or soybean protein.

7. The method of claim 1, wherein the ionic transition metal is copper(II), indium (III), tin(II) or tin(IV).

8. The method of claim 1, further comprising the step of adjusting the pH of the peptone-metal complex to about pH 6.0 to 7.0.

9. The method of claim 3, wherein the precipitate of peptone-metal complex is isolated by centrifugation.

10. The topical composition of peptone-metal complex produced by the process of claim 1.

* * * * *